United States Patent
Angeles Alvarez et al.

(10) Patent No.: US 9,474,268 B2
(45) Date of Patent: Oct. 25, 2016

(54) USE OF A HERBICIDAL COMPOSITION FOR CONTROLLING PARASITIC PLANTS

(71) Applicant: Instituto de Ecologia, A.C., Veracruz (MX)

(72) Inventors: Pedro Guillermo Angeles Alvarez, Veracruz (MX); Gregorio Cardoso Tapias Ceccantini, Sao Paulo (BR)

(73) Assignee: Instituto de Ecologia, A.C., Xalapa (MX)

( * ) Notice: Subject to any disclaimer, the term of this patent is extended or adjusted under 35 U.S.C. 154(b) by 0 days.

(21) Appl. No.: 14/122,947

(22) PCT Filed: Jan. 15, 2013

(86) PCT No.: PCT/MX2013/000007
§ 371 (c)(1),
(2) Date: Nov. 27, 2013

(87) PCT Pub. No.: WO2013/129902
PCT Pub. Date: Sep. 6, 2013

(65) Prior Publication Data
US 2014/0357488 A1    Dec. 4, 2014

(30) Foreign Application Priority Data

Feb. 27, 2012    (MX) .................... MX/a/2012/002483

(51) Int. Cl.
*A01N 57/04*      (2006.01)
*A01N 25/24*      (2006.01)
*A01N 57/20*      (2006.01)

(52) U.S. Cl.
CPC ............. *A01N 25/24* (2013.01); *A01N 57/20* (2013.01)

(58) Field of Classification Search
None
See application file for complete search history.

(56) References Cited

U.S. PATENT DOCUMENTS

| | | | |
|---|---|---|---|
| 4,152,429 A | 5/1979 | Hayakawa et al. | |
| 4,238,219 A * | 12/1980 | Holm et al. | 504/127 |
| 4,240,819 A | 12/1980 | Fritz et al. | |
| 4,352,689 A | 10/1982 | Fritz et al. | |
| 4,361,436 A | 11/1982 | McCarthy et al. | |
| 4,374,661 A | 2/1983 | Fritz et al. | |
| 4,840,660 A * | 6/1989 | Kowite et al. | 504/208 |
| 5,248,086 A | 9/1993 | Waldrum et al. | |
| 5,429,646 A | 7/1995 | Givens | |
| 6,579,830 B1 | 6/2003 | Laurie | |
| 7,192,906 B2 * | 3/2007 | Hirohara et al. | 504/280 |

FOREIGN PATENT DOCUMENTS

| AU | 764967 B | 9/2003 |
|---|---|---|
| JP | 2007244364 A | 9/2007 |

OTHER PUBLICATIONS

Livingston et al.,Effective use of ethylene-releasing agents to prevent spread of eastern dwarf mistletoe on black spruce, Can. J. For. Res. vol. 15, 1985, pp. 872-876.*
Eklund et al., Interaction between indole-3-acetic acid and ethylene in the control of tracheid production in detached shoots of Abies balsamea, 1994, Tree Physiology 15, 27-34.*
Brown, K.M. et al. Ethylene and the regulation of growth in pine, Canadian Journal of Forest Research, vol. 3, pp. 143-145, (1973).
Hawksworth and Johnson. Biology and management of dwarf mistletoe in lodgepole pine in Rocky Mountains. USDA Forest Service, General Technical Report RM-169 (1989).
Livingston W. et al. Effective use of ethylene-releasing agents to prevent spread of eastern dwarf mistletoe on black spruce, Canadian Journal of Forest Research, vol. 15, pp. 872-876, (1985).

* cited by examiner

*Primary Examiner* — Alton Pryor
(74) *Attorney, Agent, or Firm* — The Webb Law Firm

(57) ABSTRACT

The present invention relates to compositions consisting of: (a) at least one ethylene-releasing compound, and (b) at least one fatty acid ester, alone or in combination with one or more excipients, vehicles or additives, and/or (c) one or more noxious agents. The invention also relates to the use of said composition and to methods for controlling parasitic plants and/or hemiparasitic plants that cause infestations in certain trees. The composition of the invention is characterized in that it exhibits a high degree of adhesion to the parasitic and/or hemiparasitic plant is selective and acropetal, and hast excellent stability and water-impermeability, allowing the prolonged and constant release of ethylene.

3 Claims, No Drawings

US 9,474,268 B2

USE OF A HERBICIDAL COMPOSITION FOR CONTROLLING PARASITIC PLANTS

CROSS-REFERENCE TO RELATED APPLICATIONS

This application is the United States national phase of International Application No. PCT/MX2013/000007 Filed Jan. 15, 2013, and claims priority to Mexican Patent Application No. MX/a/2012/002483 filed Feb. 27, 2012, the disclosures of which are hereby incorporated in their entirety by reference.

FIELD OF THE INVENTION

This invention relates to compositions consisting of: (a) at least an ethylene-releasing compound and (b) at least a fatty acid ester, alone or combined with at least one excipient, vehicle or additive; to the use of said composition and to methods for controlling parasitic and/or hemiparasitic plants infesting certain trees. The compositions subject matter of this invention are characterized by exhibiting high degree of adhesion to parasitic plants, a high degree of water-impermeability allowing a prolonged liberation of the ethylene-releasing agent.

BACKGROUND OF THE INVENTION

It is esteemed that the number of flowering plants existing in the world over amounts to more than 250,000 species. Within the trophic chain, green or chlorophyll plants are on the basement of the pyramid as they are autotrophic, i. e., they are capable of producing their own food from inert mineral substances, such as $CO_2$ (carbon dioxide) and $H_2O$ (water), by transforming them into glucose with solar energy as an activating partner. However, there is a small group (1%=2,500 species) of plants lacking (at least partially) of the photosynthesis capability, whereby there change into heterotrophic, thus totally or partially stealing the sap elaborated by other plants; i. e., they live on the nutrients provided by other organic forms (Heywood, 1978).

Parasitic and/or hemiparasitic plants are within this group; of which more than 2500 species are known. These need to take the substance from other living organism, so-called host or lodge-giver. Botanic families with species representative of holoparasitic, strictly parasitic and/or hemiparasitic are: Santalaceae, Balanophoraceae, Rafflesiaceae, Misodendraceae, Cynomoriaceae, Hydnoraceae, Convolvulaceae (Custuta), Lauraceae (Cassytha), Lennoaceae (Lennoa), Scrophulariaceae (Striga and Castilleja), Orobanchaceae (Oribanche and Conopholis) and Loranthaceae (*Arceuthobium, Phoradendron, Psittacanthus, Struthanthus* and *Cladocolea*); the so-called mistletoe or "graft" belong to this latter family (INIFAP, 2006, Garrido, 2010).

There are very different classifications of mistletoes in the state of the art, which show how much must be learned and determined on this field. One of said classifications states that all mistletoes belong to Loranthaceae family, formed by some 40 genuses grouped into Loranthoidae (gigantic or tropical mistletoes) and Viscoidae (dwarf of tempered mistletoes) subfamilies. However, another more spread classification divides said mistletoes into two families: Loranthaceae and Viscaceae, and assigns 76 genus to the first family and 9 to the second. Both classifications agree in the existence of from 1000 to 1500 different species of mistletoes distributed in the world over. As a pair of examples, in Loranthaceae family, *Struthantus* genus comprises about 18 species, *Cladocolea* genus about 37 (although some specialists only assign 19) and *Psittacanthus* genus about 140 (or from 75 to 80, according with other experts). *Phoradendron* genus comprises about 500 species (although other specialists state that they are 300 and other more said that they are 180) and *Viscum* genus has assigned about 340 species. An evident conclusion is that the reason for said so remarkable variations is that there is an important duplication of species (synonymy), a confuse taxonomy and, in general, contradictory data revealing a lack of agreement among the specialists.

According to the Asociación Mexicana de Arboricultura (AMA), there are hundreds of species of mistletoe around the world, representing a serious problem in natural forests, plantations, fruit orchards and urban trees. In certain European countries, for instance, wherein Coniferae are predominant, *Viscum album* presence is of great importance. In the Southwestern United States, all the mistletoe (with the exception of one) belong to *Phoradendron* genus. In Chile, among other, we can find *Tristerix aphyllus*; but in the great majority of South American countries *Triodanthus acutifolius* prevails. A particular case is the city of Curitiba, Brazil, wherein about a third part of the urban trees are infested by this species which exhale such a grateful fragrance during the blossoming that all the inhabitants of said city find them adorable and are opposed to the removal of their trees (AMA, 2009).

In Mexico, parasitic plants of the Loranthaceae family are present in almost all of the natural ecosystems, there being registered presently 10 genuses and about 150 species (Chazaro et al., 1992); these plants constitute the third destruction agent in forests of cold tempered climate, after the fires and the decorticator insects, as they are present over more of the 10% of the wooded surface (Caballero, 1970), equivalent to about 1.8 million Ha of Coniferae and Latifoliae forests. Due to the parasitism of said mistletoe, a mean timber-yielding volume of 1.04 $m^3$/year/Ha is lost, representing a yearly loss, at a nation level, of about 2 million cubic meter of round timber, without taking into account the volume lost by death of the trees (Vazquez, 1993).

Some State in Mexico, mainly Veracruz, Jalisco, Chiapas and Oaxaca, have the greater flora diversity in the country, whereby the majority of the species inhabiting there favor the presence of parasitic and/or hemiparasitic plants, among which mistletoes are the more numerous species growing in branches and body of different trees (Contreras, 2000).

Mistletoes are the second biological agent in the world of disturbance in tempered climate forests, with estimated losses of millions of $m^3$ of timber by the year, without taking into account the death of on feet threes and the susceptibility to attacks by forest plagues and illnesses.

Actual studies carried out on parasitic and/or hemiparasitic plants show the presence of 10 genuses and 151 species of mistletoes distributed all over the country. As parasites on Coniferae there are reported four genuses of *Arceuthobium*, known as dwarf mistletoes and *Psittacanthus, Phoradendron* and *Struthanthus* as right mistletoes. In the case of Latifoliae or trees with broad leaves, the parasitic variety is greater, there being nine genuses the more representative of which are: *Phoradendron, Psittacanthus, Struthanthus, Cladocolea, Phthirusa, Dendrophthora, Oryctanthus, Antidaphne* and *Ixocactus*.

The damages caused by these plants to their host vary from a wood deformation, a reduced growth, a greater susceptibility to the attack by other illnesses, up to a reduction in the tree longevity.

On the other side, there are known in the state of the art and are being searched different methods for the control of said parasitic plants; among which the more important are:

1. Biologic control. It consists in developing insects or fungi as practical agents in the control of parasitic plants.

2. Forestry control. It consists in the management of infected sites and involves the detection, evaluation, prevention and suppression of the pathogen. Once the infected tree or branch are cut away, the parasitic or hemiparasitic plant dies.

3. Chemical control. The development of a selective herbicide to control parasitic and/or hemiparasitic plants; the investigation with 60 different chemical products (a majority of which were formulations of 2,4-D or 2,4,5-T), but none of them was selective enough, as they also damaged the host tree. Ethephon (2-chloroethylphosphonic acid) is the most promising chemical product to induce the abscission of the aerial portion of the parasitic and/or hemiparasitic plants, with few secondary effects on the main host, respecting the combination host-parasite and the local environmental conditions (Hawksworth & Johnson, 1989).

Ethephon® or 2-chloroethylphosphonic acid is capable of reducing the extension index of the dwarf mistletoe and protecting those trees under the infected trees. However, the compositions existing in the state of the art do not allow the healing of the infected trees while the endophytic system remains alive, whereby the application thereof is restricted to trees in high valued areas, such as recreational, residential and commercial places.

There are described in the state of the art different compositions containing Ethephon®, among which there are: a concentrated aqueous suspension containing Tidiazuron and Ethephon®, one or more surfactants, one or various thickeners and water, as well as the use thereof to defoliate cotton plants (MX 212959); a composition for controlling fungi in a plant, consisting of 20 ppm 2-chloroethylphosphonic acid and about 84 ppm methyl-1-(butylcarbamoyl)-2-benzimidazol carbamate (U.S. Pat. No. 4,152,429); a synergic combination of 2-chloroethylphosphonic acid with tetrachloroisophthalonitrile for increasing the ethylene-release into the plants tissues (U.S. Pat. No. 4,238,219); a method for inhibiting the growing of plants by applying to them 2-chloroethylphosphonic acid (U.S. Pat. No. 4,240,819 and U.S. Pat. No. 4,374,661); a method for controlling the apical dominance consisting en the application of 0.1 lb to 16 lb per acre of plants, of 2-chloroethylphosphonic acid (U.S. Pat. No. 4,352,689); a composition to regulate the growing of a plant, containing 2-chloroethylphosphonic acid and a N-heterocyclic amine (U.S. Pat. No. 4,361,436); a stable composition to regulate the growing of plants, comprising a dispersion in the shape of a microemulsion and containing micelles of no more than 300 nm diameter, with 2-chloroethylphosphonic acid, hydrocarbon oil, water and hydrophobic surfactant (U.S. Pat. No. 4,840,660); an Ethephon® emulsion with 15 to 50% oil phase and 50 to 80% aqueous phase to be applied as a spray (U.S. Pat. No. 5,248,086).

On the other side, the state of the art discloses some methods for the control of mistletoe, including a method to eliminate mistletoe from branches of host plants by using a material o opaque plastic to cover said branch until the death thereof; then remove said branch (U.S. Pat. No. 5,429,646 and JP 2007244364); a process for the control of mistletoe in host plants by applying to said mistletoe natural oils as a physical barrier to interrupt the carbon dioxide and water consumption (U.S. Pat. No. 6,579,830), among other methods.

SUMMARY OF THE INVENTION

This novel invention relates to new compositions containing (a) at least an ethylene-releasing compound, and (b) at least a fatty acid ester, alone or combined with one or more excipients, vehicles or additives and, in an optional and non-limitative manner, one or more enzymatic agents (c); as well as the use of said composition and methods for the control of parasitic and/or hemiparasitic plants, such a mistletoe, infesting host plants. The compositions subject matter of the present invention are characterized by exhibiting a high adherence to the parasitic and/or hemiparasitic plant; efficacy and efficiency in the control of said parasitic and/or hemiparasitic plant; a high water impermeability and a controlled and constant release of the ethylene-releasing agent, further providing for an acropetal highly selective and directional application.

DETAILED DESCRIPTION OF THE INVENTION

This invention relates to a composition containing: (a) at least an ethylene-releasing compound and (b) at least a fatty acid ester, alone or combined with one or more excipients, vehicles or additives and in an optional and non-limitative manner, one or more enzymatic agents (c).

This novel composition disclosed in the present document is characterized by exhibiting high stability under environmental conditions at open air, maintaining the properties of the ethylene-releasing agent. This allows that said novel composition is efficient and effective in the different zones where the plants are infested by parasitic and/or hemiparasitic plants, such as mistletoe.

The ethylene-releasing agent used in the present invention is Ethephon®, also known as ethephon, Ethrel® or 2-chloroethylphosphonic acid, which is reported in the state of the arte for controlling mistletoe; however, it has a serious disadvantage: that the existing compositions cannot be maintained permanent on the plants during and after the application thereof; whereby said active agent is rapidly eliminated from the plant by means of air of rain, thus diminishing the efficacy and efficiency thereof in the control of mistletoe.

The composition of this invention solves the problem of the existing compositions of the state of the art, by obtaining a composition with high adherence, stability and water-impermeability, through the addition of a fatty acid ester combined with the ethylene-releasing agent.

It is a basic characteristic of the composition of this invention that the fatty acid ester employed, in a descriptive but non-limitative manner, is a lanoline, that allows a homogeneous dispersion of the ethylene-releasing agent at different concentrations; and being compatible with each other, whereby said composition provides a surprising stability during the storage and use.

Another unexpected characteristic of the composition is that, due to the use of lanolin, a high adherence is obtained, thus providing for the permanence of the composition on the parasitic plant for up to 50 days.

The mechanism of action of the composition is based on the adherence thereof to the parasitic and/or hemiparasitic plant and on the continuous and prolonged release of said ethylene-releasing agent, directly into the parasitic plant, thus interrupting the water and sugars conduction to the parasitic and/or hemiparasitic plant, whereby the latter are deadly damaged in an effective manner within a period of time lesser than 50 days, and being maintained adhered thereto until said parasitic and/or hemiparasitic plant is completely eliminated. Furthermore, said composition is water-impermeable and, therefore, it remains adhered to the parasitic plant even under conditions of high humidity or event under the effects or rain or snow.

Under the light of this investigation, different concentrations of Ethephon® in lanoline were assayed: 2, 4, 6, 8 and 10 percent w/w. These were applied around stalks of *Psittacantus schiedeanus* parasiting on a *Liquidambar styraciflua*. Said stalks were examined once a week and it was found that at a concentration of 10 percent w/w, the effect was faster, making that within 30 to 45 days, the distal end of the treated branches of *Psittacanthus schiedeanus* reached necrosis.

The developed method for controlling parasitic and/or hemiparasitic plants consists of: applying directly to the stem, leaves and/or flowers of a parasitic and/or hemiparasitic plant, either manually or by means of a device or equipment specially designed for the application thereof and the obtaining of the desired effect. An amount of from 1 g and 100 g of said composition is to be applied.

As an alternative to the method disclosed in the previous paragraph, a method can be employed consisting of: damaging the cuticle covering the epidermis of a parasitic and/or hemiparasitic plant; through this damage the elimination of the parasitic and/or hemiparasitic plant is obtained within 10 to 20 days maximum. Said cuticle damage can be effected either by small oblique cuttings on the surface of the stalk, by using a knife, or slightly scratching said cuticle with a mean grain sandpaper, as well as by any other mechanical, chemical, enzymatic, biological manner, or by means of some device or equipment. Both treatments were used previous to the application of the lanolin paste with 10% Ethrel®. The damage to the cuticle without the application of Ethephon® or by applying only lanoline, caused no damage at all to the treated branch; which means that the combination of said methods acts in a synergic manner for the control of parasitic and/or hemiparasitic plants.

It is to be mentioned that these same treatment, applied to the plant (*Liquidambar styraciflua*, in the case) harboring the parasite also caused the necrosis of the distal portion of the treated branches. Due to this, it is necessary to apply carefully said composition carefully in order to avoid damages to the host plant.

Further to the ethylene-releasing agent and the fatty acid ester, one or more excipients, vehicles or additives can be added to the composition in order to improve the characteristics of the composition; these ingredients can be: water, alcohols, organic solvents, inorganic solvents, surface-active agents, thickeners, moisteners, surfactants, defoamers, emulsifiers, cosolvents, organic acids, inorganic acids, preservers, antifreezers, greases, polymers, polyethylene glycol, Vaseline, white and yellow waxes, whale sperm, vegetal or animal oils (almold, peanut, olive, sesame), colorants, pH controllers, celluloses and/or combinations thereof.

This composition also can or cannot contain one or more agents that increase the damage activity to the parasitic and/or hemiparasitic plant and/or that protect the host plant, among which there are: thidiazuron, natural oils, gums, methyl-1-(butylcarbamoyl)-2-benzimidazol-carbamate, polysaccharides, tetrachloroisophthalonitrile, N-methylpirrolidone, pirrolidone, polyvinylpirrolidone, N-methylpiperidone, 2-haloethylphosphonic acids, anhydrides, catechol 2-haloethylphosphonic esters, malonic acid derivatives, microorganisms, fosetyl-Al, 3-(3-methyl-4-chlorofenoxy) butyric acid, diflufenzopyro, ethyl-hexanol, alkoxylate, nitroguanidin, cyanoguanidin, S-abscisic acid, sodium humate, ammonium nitrate, urea, maleic hydrazide, paclobutrazol, uniconazol, cicocel, mepiquat chloride, triapenthenol, daminozide, taterpex, 2-iodo-N-[4-methoxy-6-methyl-1,3,5-triazin-2-yl) carbamoyl)-benzensulfonamide, 6-benzyl-amine-purine, imidacloprod, dymuron, 1,3-diphenylurea, 8-decene-1,10-dicarboxylic acid, acylcyclohexadione derivatives, 4-cyclopropyl-3,5-cyclohexadione-1-carboxylic acid, diflufenzopir, Cyanamid, benzyladenine, epoxycyclohexan, gibereline, polyalkyls, N-acylethanolamine, gentianose inhibitors and/or combinations thereof.

Alternatively the composition may include one or more enzymes acting on the parasitic plants tissues, increasing the damage and thus eliminating said plant more rapidly, for both obtain greater efficacy and efficiency and reduce the noxious effects provoked on the host plant.

The application of the composition hereof acts on those parasitic plants infecting any host plant; in a descriptive, non-limitative manner, these can be: *Liquidambar styraciflua, Quercus* spp., *Platanus mexicana*, several citric, *Pinus hart wegii, Pinus montezumae, Persea americana, Mangifera indica, Eucalyptus* spp., *Casuarina* spp., *Theobroma cacao, Coffea arabica, Hevea brasiliensis, Erytrhina mexicana*, apple tree, peach tree walnut tree, etc.

Now examples of the compositions obtained during the development of the present invention are given herein in an illustrative but non-limitative manner:

EXAMPLES

Example 1

Composition with 2% Ethephon®

| INGREDIENT | AMOUNT |
| --- | --- |
| 2-ethylphosphonic acid | 2 g |
| Lanolin | q.s. 100 g |

Example 2

Composition with 4% Ethephon®

| INGREDIENT | AMOUNT |
| --- | --- |
| 2-ethylphosphonic acid | 4 g |
| Lanolin | q.s. 100 mL |

Example 3

Composition with 6% Ethephon®

| INGREDIENT | AMOUNT |
| --- | --- |
| 2-ethylphosphonic acid | 6 g |
| Lanolin | q.s. 100 g |

Example 4

Composition with 8% Ethephon®

| INGREDIENT | AMOUNT |
|---|---|
| 2-ethylphosphonic acid | 8 g |
| Lanolin | q.s. 100 g |

Example 5

Composition with 10% Ethephon®

| INGREDIENT | AMOUNT |
|---|---|
| 2-ethylphosphonic acid | 10 g |
| Lanolin | q.s. 100 g |

Example 6

Composition with 10% Ethephon®

| INGREDIENT | AMOUNT |
|---|---|
| 2-ethylphosphonic acid | 10 g |
| Surfactant | 1 g |
| Lanolin | q.s. 100 g |

Example 7

Composition with 10% Ethephon®

| COMPONENT | AMOUNT |
|---|---|
| 2-ethylphosphonic acid | 10 g |
| Enzime | 1 g |
| Lanolin | q.s. 100 g |

Example 8

Composition with 10% Ethephon®

| Component | Amount |
|---|---|
| 2-ethylphosphonic acid | 10 g |
| Enzime | 1 g |
| Surfactant | 1 g |
| Lanolin | q.s. 100 g |

In an integral manner, the present invention provides the following advantages:

1. A composition for the control of parasitic and/or hemiparasitic plants.
2. A composition acting on parasitic and/or hemiparasitic plants in lesser than 50 days.
3. A composition that remains settled on the parasitic and/or hemiparasitic plant until the death thereof.
4. A water impermeable composition that can be used in high humidity conditions and during rain seasons.
5. A composition having excellent stability under storage and use conditions.
6. An economic process composition.
7. A highly selective and directional acropetal composition.
8. A low cost method of controlling parasitic and/or hemiparasitic plants.
9. An efficient and effective method of controlling parasitic and/or hemiparasitic plants.
10. The use on ornamental or agricultural production host plants.

Once disclosed the invention, it is claimed as a property the contents of the following claims.

The invention claimed is:

1. A method for the control of a parasitic plant, comprising applying a composition comprising 1-25% w/w of 2-chloroethylphosphonic acid and 75-99% w/w of lanolin and optionally one or more damage agents directly to a parasitic plant on a host plant, wherein the parasitic plant is one that infects a host plant selected from the group consisting of *Liquidambar styraciflua*, *Quercus* spp., *Platanus mexicana*, *Pinus hartwegii*, *Pinus montezumae*, *Persea americana*, *Mangifera indica*, *Eucalyptus* spp., *Casuarina* spp., *Theobroma cacao*, *Coffea arabica*, *Hevea brasiliensis*, *Erytrhina mexicana*, citrus, apple, peach and walnut.

2. The method according to claim 1, wherein the composition further includes a mechanical, chemical, biologic or enzymatic agent to damage a cuticle of the parasitic plant.

3. The method according to claim 1, wherein the method further comprises applying the composition in a highly selective and directionally acropetal application to a parasitic plant.

* * * * *